United States Patent [19]

Kuruvilla et al.

[11] Patent Number: 5,693,869
[45] Date of Patent: Dec. 2, 1997

[54] PROCESS FOR THE SINGLE STEP OXIDATION OF 3-PHENOXYTOLUENE TO 3-PHENOXYBENZALDEHYDE

[75] Inventors: Joseph Kuruvilla; Changaramponnath Gopinathan; Sarada Gopinathan; Paul Ratnasamy, all of Pune, India

[73] Assignee: Council of Scientific & Industrial Research, India

[21] Appl. No.: 353,818

[22] Filed: Dec. 9, 1994

[51] Int. Cl.$^6$ ........................................... C07C 45/28
[52] U.S. Cl. .................................. 568/432; 568/426
[58] Field of Search ........................... 568/426, 432

[56] References Cited

U.S. PATENT DOCUMENTS

| | | | |
|---|---|---|---|
| 3,946,067 | 3/1976 | Kwiatek et al. | 260/476 |
| 4,054,607 | 10/1977 | Matswoka et al. | 260/600 |
| 4,366,325 | 12/1982 | Wedemeyer et al. | 568/432 |
| 4,429,163 | 1/1984 | Nishizawa et al. | 568/432 |
| 4,700,009 | 10/1987 | Nosberger | 568/431 |
| 4,814,512 | 3/1989 | Ueshima et al. | 568/431 |
| 4,929,766 | 5/1990 | Schnatterer et al. | 568/432 |
| 5,136,104 | 8/1992 | Saito et al. | 568/431 |
| 5,354,919 | 10/1994 | Costantini et al. | 568/432 |
| 5,576,463 | 11/1996 | Schnatterer et al. | 568/431 |

*Primary Examiner*—Kimberly J. Prior
*Attorney, Agent, or Firm*—Schweitzer Cornman Gross & Bondell LLP

[57] ABSTRACT

This invention relates to an improved process for the single step oxidation of 3-phenoxytoluene to 3-phenoxybenzaldehyde using molecular oxygen as the oxidant by employing a $Ti_2VMoP_6O_{24}$ catalyst having particular infrared spectral bands.

8 Claims, No Drawings

PROCESS FOR THE SINGLE STEP OXIDATION OF 3-PHENOXYTOLUENE TO 3-PHENOXYBENZALDEHYDE

This invention relates to an improved process for the single step oxidation of 3-phenoxytoluene to 3-phenoxybenzaldehyde using molecular oxygen as the oxidant.

BACKGROUND AND SUMMARY OF THE INVENTION

3-Phenoxybenzaldehyde is an intermediate for Fenvalerate and several other synthetic pyrethroids like Cypermethrin, Deltamethrin, Flycythrin and Fluvalinate. It can be hydrogenated to the corresponding alcohol, namely 3-phenoxybenzyl alcohol, which is the intermediate for Permethrin. Permethrin is used as a broad spectrum insecticide for cotton and other field crops.

3-Phenoxybenzaldehyde can be obtained from 3-phenoxytoluene by various routes. In one route of the prior art in commercial practice, the phenoxytoluene is first chlorinated to the phenoxybenzyl chloride. The chloride is then treated with a mixture of formaldehyde and ammonia in the presence of water and ethanol. The next step consists of the acidification of the above components. The reactions leading to the formation of 3-phenoxybenzaldehyde are:

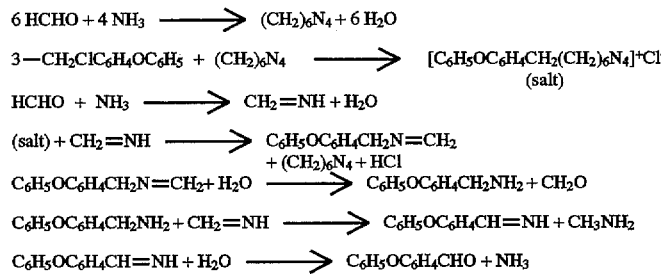

This process has many disadvantages including handling of large amounts of chlorine, a number of unwanted side reaction products such as the corresponding benzal chlorides and compounds in which the benzene rings are directly chlorinated.

Methods for the direct oxidation of 3-phenoxytoluene to 3-phenoxybenzaldehyde are also known in the prior art. Japanese Patents 55-23812 (1980) and 58-50204 (1983) teach that the liquid phase oxidation of 3-phenoxytoluene by oxygen in alcohol and/or in acetic anhydride in presence of a bromide, a cobalt salt and a co-oxidizing agent such as benzaldehyde gives 3-phenoxybenzaldehyde with less 3-phenoxybenzyl alcohol and a little 3-phenoxybenzyl acetate.

British Patent 1,579,702 (1980) describes the oxidation of 3-phenoxyltoluene to 3-phenoxybenzaldehyde at 330°–340° C. in the presence of an oxide of vanadium, antimony or molybdenum.

Japanese Patent 56-20539 (1981) claims the oxidation of 3-phenoxytoluene over $K_2S_2O_8$.

Japanese Patent 56-57723 (1981) claims the oxidation of 3-phenoxytoluene with alkali chloride as catalyst.

Japanese Patent 56-108728 (1981) claims the air oxidation of 3-phenoxyltoluene at 70° C. with bromides of Co-Mn-Zn catalysts and with a selectivity of around 59%.

The electrochemical oxidation of 3-phenoxytoluene as well as oxidation using a mixture of cobalt acetate-lithium bromide as catalysts is also known in the prior art.

The processes described above have to cope up with the multi step operation and/or poor selectivity coupled with waste disposal problems. Hence there is a genuine need for an improved catalyst with higher selectivity and less waste disposal problems.

DETAILED DESCRIPTION OF THE INVENTION

It is an objective of the present invention to provide a convenient, environmentally cleaner and safer process for the direct, single step oxidation of 3-phenoxytoluene to 3-phenoxybenzaldehyde using molecular oxygen as the oxidant and a solid, as heterogeneous catalyst.

Accordingly, the present invention provides an improved process for the oxidation of 3-phenoxytoluene which comprises contacting the said 3-phenoxytoluene in the vapour phase with molecular oxygen in the presence of a solid catalyst composite material containing a compound with a chemical composition of $Ti_2VMoP_6O_{24}$ having characteristic infrared spectral bands shown in Table 1. The compound is a phosphate of titanium, vanadium and molybdenum.

TABLE 1

CHARACTERISTIC INFRA-RED ABSORPTION BANDS OF THE CATALYST IN THE M–O STRETCHING REGION

| Catalyst | in $cm^{-1}$ (% intensity) | | | | |
|---|---|---|---|---|---|
| 1. | 1098 (98) | 965 (52) | 730 (16) | 625 (11) | 560 (20) |
| 2. | 1102 (96) | 967 (48) | 732 (15) | 620 (10) | 562 (21) |
| 3. | 1100 (97) | 966 (50) | 735 (17) | 626 (11) | 561 (22) |

In the prior art, metal oxides are usually the preferred catalysts to oxidize alkyl groups attached to aromatic rings to the corresponding aldehydes. British Patent 1,579,702 in fact has discussed the use of metal oxides, wherein the metal is vanadium, niobium, tantalum, antimony, bismuth, chromium, molybdenum or tungsten, in the air oxidation of 3-phenoxytoluene to 3-phenoxybenzaldehyde.

Mixed phosphates of titanium and vanadium are well known catalysts in the prior art for Aldol condensation reactions. German Patent 1,294,956 (1970), for example, claims the use of such titanium-vanadium phosphates in the manufacture of unsaturated carboxylic acids by the vapour phase Aldol condensation reaction:

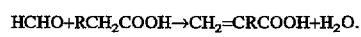

$HCHO+RCH_2COOH \rightarrow CH_2=CRCOOH+H_2O$.

It was, hence, a surprising and unanticipated observation during the course of our investigations leading to the present invention, that such mixed metal phosphates of titanium, vanadium and molybdenum were found to be highly selective catalysts for the direct oxidation of 3-phenoxytoluene using molecular oxygen as the oxidant.

In one embodiment of the process of the present invention, the temperature at which the oxidation is carried out suitably lies in the range of 300° to 500° C., preferably around 400° C.

The process is preferably carried out at atmospheric pressure.

In another embodiment, the molecular oxygen may be in the form of air, care being taken that its concentration in the reaction mixture is below the explosion limits.

In yet another embodiment, the catalyst composite material containing $Ti_2VMoP_6O_{24}$ is in the form of a fluidized bed, the gas hourly space velocity through the bed being adequate to keep the catalyst bed in the fluidized form.

The catalyst composition material may contain the compound $Ti_2VMoP_6O_{24}$ alone or it may optionally contain some binder which will improve its mechanical properties.

This invention is further described with reference to the following examples. Examples 1 and 2 describe the preparation of the catalysts used in the process of the present invention and Examples 3–5 illustrate the process of the present invention.

EXAMPLE 1

Titanium tetrachloride (38 g) was added drop by drop to chilled 85% phosphoric acid (70 g) under constant stirring. The viscous material was heated slowly till all HCl gas was expelled. Ammonium metavanadate (11.7 g) and ammonium molybdate (17.65 g) were dissolved in 30% oxalic acid (200 ml) and boiled till the entire solution turned deep blue indicating the presence of reduced vanadium ion. This solution was added to the slurry of phosphoric acid containing titanium phosphate under vigorous stirring. The slurry was then evaporated to get a uniform dry solid mass which was further dried in a stream of air at 275°–300° C. for 8 hrs, and again at 450° C. for another 8 hrs. The resulting dry mass was crushed and sieved to the required mesh size. The solid was a phosphate of vanadium, titanium and molybdenum. The chemical composition was $Ti_2VMoP_6O_{24}$. The surface area by the BET method was 42 $m^2/g$.

EXAMPLE 2

Titanium tetrachloride (38 g) was dissolved in chilled water and hydrolized with ammonia solution. The gel formed was filtered and washed with water till chloride free. The resulting gel of hydrated titanium dioxide was added to 85% phosphoric acid (70 g) and mixed to get a uniform mass. A mixture of ammonium metavanadate (11.7 g) and ammonium molybdate (17.65 g) were dissolved in 30% oxalic acid (200 ml) and monoethylene glycol (50 ml) was added and the solution boiled till it became deep blue. This was mixed with the titanium phosphate slurry and evaporated to dryness at 130°–140° C. and then at 275°–300° C. in a current of air for 8 hrs. and finally at 450° C. for another 8 hrs. The resulting material had a chemical composition $Ti_2VMoP_6O_{24}$, a surface area of 38 $m^2/g$ and exhibited the infrared spectral bands as in Table 1.

EXAMPLE 3

Oxidation of 3-phenoxy toluene was carried out in a fluidized bed reactor containing 25 g of catalyst made as in Example 1. The temperature was 450° C., feed rate of phenoxytoluene 15 ml/hr, air 25 liters/hr and nitrogen 20 liters/hr. The conversion was 21% and the selectivity to 3-phenoxybenzaldehyde was 75%. Products other than phenoxybenzaldehyde were toluene, benzaldehyde, diphenyl ether and carbon dioxide. The carbon dioxide formed was as low as 2% of the phenoxytoluene converted.

EXAMPLE 4

In another example the oxidation was carried out at 400° C. in a fluidized bed. Rate of feeding phenoxy toluene was 10 ml/hr, air 30 L/hr, nitrogen 15 L/hr conversion 15.5%, and selectivity 72%.

EXAMPLE 5

In yet another example, 25 g of catalyst in extrudate form was used in a vertical reactor. The reaction was carried out in a static bed with the downward flow of reactants and and products. In an experiment, phenoxytoluene (5 ml/hr) was fed through a syringe pump. A mixture of air (2 L) and nitrogen (3 L) was passed through the bed maintained at 400° C. Computation of product analysis showed a conversion of 12% and selectivity of 62%.

We claim:

1. An improvement in a process for the oxidation of 3-phenoxytoluene to 3-phenoxybenzaldehyde, the improvement comprising carrying out the oxidation in the vapor phase by contacting 3-phenoxytoluene at a temperature between 300° C. and 500° C. with oxygen in the presence of a composite catalyst which comprises the compound $Ti_2VMoP_6O_{24}$ and having the following infrared absorption bands in the M-O stretching region

| 1 | 1098(98) | 965(52) | 730(16) | 625(11) | 560(20) |
|---|----------|---------|---------|---------|---------|
| 2 | 1102(96) | 967(48) | 732(15) | 620(10) | 562(21) |
| 3 | 1100(97) | 966(50) | 735(17) | 626(11) | 561(22). |

2. A process as claimed in claim 1, wherein the catalyst composite material is in the form of a fluidized or static bed.

3. An improved process as claimed in claim 1, wherein the reaction is effected at atmospheric pressure.

4. An improved process as claimed in claim 1, wherein the molecular oxygen is in the form of air.

5. An improved process as claimed in claim 1, wherein the catalyst contains a binder.

6. The improved process of claim 5, wherein said binder is catapol, or kieselguhr.

7. The improved process of claim 1, wherein said temperature is about 400° C.

8. The improved process of claim 1, wherein the reaction is carried out at a WHSV of between 1 and 5.

* * * * *